US009708580B2

(12) United States Patent
Hong

(10) Patent No.: US 9,708,580 B2
(45) Date of Patent: Jul. 18, 2017

(54) BACTERIAL CULTURE MEDIA AND METHODS FOR THEIR PREPARATION AND USE

(75) Inventor: Feng Hong, Shanghai (CN)

(73) Assignee: SHANGHAI ZHIYI INFORMATION TECHNOLOGY LTD., Shanghai (CN)

( * ) Notice: Subject to any disclaimer, the term of this patent is extended or adjusted under 35 U.S.C. 154(b) by 289 days.

(21) Appl. No.: 13/885,390

(22) PCT Filed: May 15, 2012

(86) PCT No.: PCT/CN2012/075508
§ 371 (c)(1),
(2), (4) Date: May 14, 2013

(87) PCT Pub. No.: WO2013/170440
PCT Pub. Date: Nov. 21, 2013

(65) Prior Publication Data
US 2014/0024075 A1 Jan. 23, 2014

(51) Int. Cl.
C12N 1/22 (2006.01)
C12P 19/04 (2006.01)
C12N 1/20 (2006.01)
C12P 19/14 (2006.01)

(52) U.S. Cl.
CPC ............... C12N 1/22 (2013.01); C12N 1/20 (2013.01); C12P 19/04 (2013.01); C12P 19/14 (2013.01)

(58) Field of Classification Search
CPC ............ C12N 1/22; C12N 1/20; C12P 19/04
See application file for complete search history.

(56) References Cited

U.S. PATENT DOCUMENTS

| 5,962,277 | A  | * | 10/1999 | Watanabe et al. | ............ 435/101 |
| 2009/0093027 | A1 | * | 4/2009 | Balan et al. | .................... 435/99 |
| 2009/0269832 | A1 | * | 10/2009 | Jarrell | ..................... C12N 1/16 435/252.5 |
| 2011/0217746 | A1 | * | 9/2011 | Jonsson et al. | ............... 435/165 |

FOREIGN PATENT DOCUMENTS

| CN | 101012442 A | 8/2007 |
| CN | 101113418 A | 1/2008 |
| CN | 101781666 | 7/2010 |
| CN | 101781667 | 7/2010 |
| CN | 101781668 | 7/2010 |
| CN | 102260715 | 11/2011 |
| PL | WO 2005003366 A1 * | 1/2005 ............. A61L 15/28 |

OTHER PUBLICATIONS

Ishihara et al. "Utilization of D-xylose as carbon source for production of bacterial cellulose." (2002) Enzyme and Microbial Technology, vol. 31: 986-991.*

Balan et al. "Lignocellulosic Biomass Pretreatment Using AFEX" (2009), Biofuels: Methods and Protocols, Methods in Molecular Biology, vol. 581: 61-77.*
Liang et al. "Use of dry-milling derived thin stillage for producing eicosapentaenoice acid (EPA) by the fungus Pythium irregulare" (Feb. 2012) Bioresource Technology, vol. 111: 404-409.*
Palmqvist et al. "Fermentation of lignocellulosic hydrolysates: I: inhibition and detoxification" (2000) Bioresource Technology, vol. 74, 17-24.*
Bae et al, "Bacterial cellulose production by fed-batch fermentation in molasses medium." Biotechnol. Prog. 20, 1366-1371, 2004.
Bielecki et al., Polysaccharides I: Polysaccharides from Prokaryotes), Wiley-VCH Verlag, Weinheim 2002, vol. 5, pp. 37-46.
Brown, "U.S. Corn Production and Use for Fuel Ethanol, 1980-2009." Plan B 4.0: Mobilizing to Save Civilization, New York: W.W. Norton & Company, 2009, found at https://docs.google.com/spreadsheet/ccc?key=0AonYZs4MzIZbdEpoN0t5MFZR-UENvNFdHWGNPaI94dIE&hl=en#gid=0, accessed on Mar. 20, 2013.
Distillers grains, Wikipedia. information was available at website: http://en.wikipedia.org/wiki/Distillers_grains in some form no later than Feb. 21, 2012. While a copy of the website as it existed on Feb. 21, 2012, is not in Applicant's possession, Applicant has provided a copy of the website that was printed on Mar. 7, 2013.
Goelzer et al., "Production and characterization of nanospheres of bacterial cellulose from Acetobacter xylinum from processed rice bark." Mater. Sci. Eng. C 29, 546-551, 2009.
Hong et al., An Alternative carbon source from konjac powder for enhancing production of bacterial cellulose in static cultures by a model strain *Acetobacter aceti* subsp. *xylinus* ATCC 23770. Carbohyd. Polym. 72, 545-549, 2008.
Hong et al., "Wheat straw acid hydrolysate as a potential cost-effective feedstock for production of bacterial cellulose." J. Chem. Technol. Biotechnol. 86, 675-680, 2011.
Kurosumi et al., "Utilization of various fruit juices as carbon source for production of bacterial cellulose by Acetobacter xylinum NBRC 13693." Carbohyd. Polym. 76, 333-335, 2009.
International Search Report dated Feb. 28, 2013 in International Application No. PCT/CN2012/075508.
Lehman et al, Microbial development in distillers wet grains produced during fuel ethanol production from corn (*Zea mays*)) Can. J. Microbiol. 53: 1046-1052, 2007.
Keshk et al., "Bacterial Cellulose Production from Beet Molasses" African Journal of Biotechnology vol. 5 (17), pp. 1519-1523, Sep. 4, 2006.
Shen et al., "Fermentation of Lixivium of Distiller's Grains for Bacterial Cellulose Preparation." Food Science 2010, vol. 31, No. 3 pp. 203-206 (http://en.cnki.com.cn/Article_en/CJFDTOTAL-SPKX201003045.htm).
Thompson et al., "Production of bacterial cellulose from alternate feedstocks." Appl. Biochem. Biotechnol. 91-93, 503-513, 2001.

(Continued)

Primary Examiner — Teresa E Knight
(74) Attorney, Agent, or Firm — Dorsey & Whitney LLP

(57) ABSTRACT

Provided herein are methods and compositions for bacterial cellulose production. In some embodiments, the methods and compositions involve or are made from distiller's grain.

16 Claims, 2 Drawing Sheets

(56) References Cited

OTHER PUBLICATIONS

Uraki et al., "Bacterial cellulose production using monosaccharides derived from hemicelluloses in water-soluble fraction of waste liquor from atmospheric acetic acid pulping." Holzforschung 56, 341-347, 2002.

Wang et al., "Xylitol production with fermentation of lees hydrolysate by Candidate tropicalis." China Brewing. Mar. 20, 2006, No. 156, pp. 44-47.

* cited by examiner

BACTERIAL CULTURE MEDIA AND METHODS FOR THEIR PREPARATION AND USE

CROSS-REFERENCE TO RELATED APPLICATION

This application is a U.S. National phase entry under 35 U.S.C. §371 of PCT/CN2012/075508, filed on May 15, 2012, the entire disclosure of which is hereby incorporated by reference herein.

TECHNICAL FIELD

Embodiments herein generally relate to compositions, manufactures, and methods of use involving Distiller's grain and products thereof.

BACKGROUND

Bacterial cellulose is an extracellular biomaterial produced in a microbial fermentation process. A variety of methods exist for bacterial cellulose production. Traditionally, such methods require expensive feedstocks and give low yields of bacterial cellulose.

SUMMARY

In some embodiments, methods and compositions are provided for bacterial cellulose production.

In some embodiments, a method of making culture medium for bacteria is provided. The method can include providing distiller's grain from alcohol fermentation and mixing the distiller's grain with at least one hydrolytic catalyst. In some embodiments, a hydrolysate is formed from the distiller's grain by the hydrolytic catalyst, thereby making a culture medium.

In some embodiments, a method of producing bacterial cellulose is provided. The method can include inoculating at least one bacterium in a culture medium. The culture medium can include a distiller's grain. The method can further include cultivating the at least one bacterium in the culture medium to produce bacterial cellulose, and harvesting the bacterial cellulose.

In some embodiments, a culture medium for bacterial cellulose production is provided. The medium can include at least one of a maize alcohol fermentation filtrate, a maize alcohol fermentation supernatant, a distiller's grain filtrate, a distiller's grain supernatant, a distiller's grain hydrolysate, or a detoxified distiller's grain hydrolysate. The medium can further include a carbon source, a nitrogen source, and a salt source.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
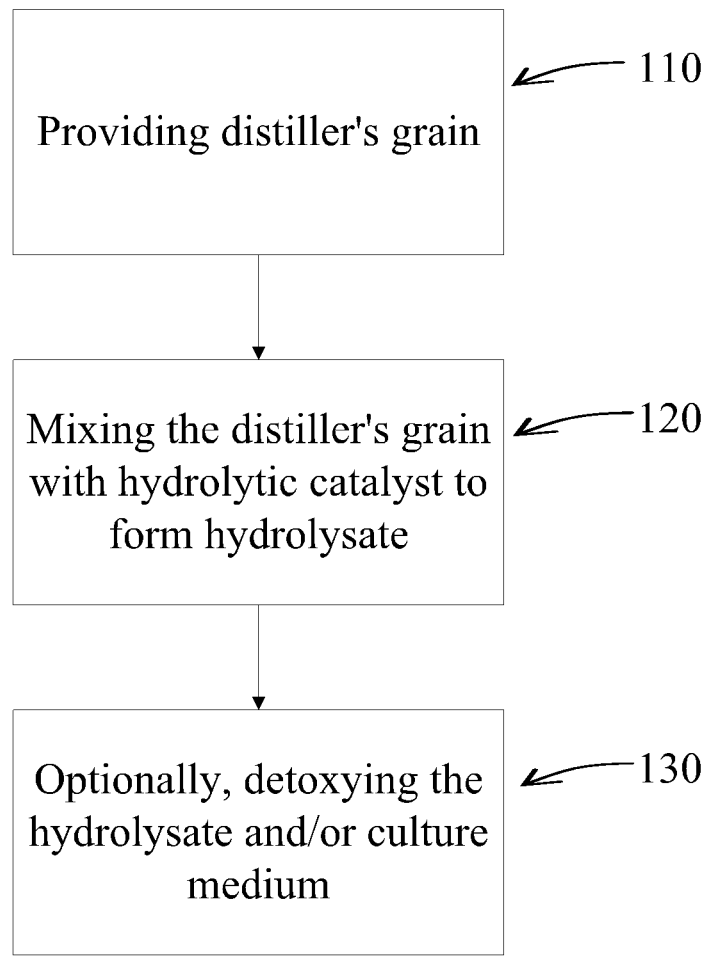
FIG. 1 is a flowchart depicting some embodiments of a method of making culture medium for bacterial cellulose production.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Provided herein are embodiments related to culture medium for bacteria. In some embodiments, the culture medium can be used for the production of bacterial cellulose. In some embodiments, the culture medium can be made from distiller's grain and/or derivatives thereof. In some embodiments, the distiller's grain can be mixed with a catalyst to form a hydrolysate, which can then be used to make a culture medium.

FIG. 1 outlines some embodiments of making a culture medium for bacterial cellulose production (FIG. 1). The method can include providing distiller's grain (block 110). While the distiller's grain can be from a variety of sources, the distiller's grain can be from the resulting organic material from an alcohol fermentation process. In some embodiments, the method further includes mixing the distiller's grain with at least one hydrolytic catalyst (block 120). The hydrolytic catalyst forms a hydrolysate from the distiller's grain. This hydrolysate, and other processed forms of the distiller's grain, can be employed as a culture medium for bacteria. In some embodiments, the bacteria to be cultured in such a media is a bacterium that produces bacterial cellulose. In some embodiments, the method optionally includes detoxifying the hydrolysate (block 130). The hydrolysate containing section can then be used as a culture medium for bacteria.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

As noted above, while a variety of distiller's grains can be employed, in some embodiments, the distiller's grain is a byproduct of a distillation process. In some embodiments, the distiller's grain is the solid material remaining after a fermentation. In some embodiments, the distiller's grain can be a byproduct of an alcohol fermentation. In some implementations, the distiller's grain is a byproduct of a maize ethanol fermentation. In some embodiments, the distiller's grain can be wet or dried. In some embodiments, the distiller's grain (for example, the material to be used as the starting material for subsequent hydrolytic processing) can include a wet distiller's grain (WDG), a dried distiller's grain (DDG), a dried distiller's solubles (DDS), and dried distiller's grain with solubles (DOGS), or any combination thereof. In some embodiments, the distiller's grain includes at least one of: fat, heavy metal ions, and cellulose, hemicellulose and protein. In some embodiments, the distiller's grain includes residual ethanol.

In some embodiments, the distiller's grain is treated after the fermentation. In some embodiments, the treatment can include at least one of separating, filtering, centrifuging, dehydrating, or drying of the distiller's grain and/or hydrolysate thereof.

In some embodiments, treatment of the distiller's grain produces at least one of a maize alcohol fermentation filtrate, a maize alcohol fermentation supernatant, a distiller's grain filtrate, a distiller's grain supernatant, a distiller's grain hydrolysate, or a detoxified distiller's grain hydrolysate. In some embodiments, the filtrate or supernatant can be collected. In some embodiments, the filtrate or supernatant can be assayed for carbon source content. In some embodiments, the assay can be by 3,5-dinitrosalicylic acid (DNS) method using D-glucose as a standard.

In some embodiments, at least one hydrolytic catalyst can be used for processing the distiller's grain, to thereby form a hydrolysate. In some embodiments, the at least one hydrolytic catalyst can include at least one of an acid and an enzyme. In some embodiments, the hydrolytic catalyst hydrolyzes lignocellulose, (for example, cellulose, hemicellulose and/or lignin) to sugar. In some embodiments, the hydrolytic catalyst hydrolyzes protein to amino acids.

In some embodiments, the at least one hydrolytic catalyst can be an acid catalyst. In some embodiments, the acid can be sulfuric acid, hydrochloric acid, phosphoric acid, acetic acid, citric acid, or any combination thereof. In some embodiments, the concentration of the acid is about 0.3% (w/v) to about 7% (w/v), e.g., a concentration of 0.3%, 1%, 4%, 5%, 6%, or 7%, including any range between any two of the proceeding values.

In some embodiments, the at least one hydrolytic catalyst can be an enzymatic catalyst. In some embodiments, the enzyme can include at least one of cellulase, hemicellulase, xylanase, protease, lipase, amylase, glucan glucohydrolase, and glucoamylase.

In some embodiments, in addition to including a processed distiller's grain product, the culture medium can also include a carbon source, a nitrogen source, and a salt source. In some embodiments, the culture medium includes a trace element, such as calcium, sodium, magnesium, iron, and/or zinc. In some embodiments, the method can include adding at least one of a carbon source, a nitrogen source, a salt source, and a trace element source. In some embodiments, the hydrolysate itself can provide at least one of a carbon source, a nitrogen source, a salt source, and/or a trace element source. In some embodiments, an additional amount of a carbon source, a nitrogen source, a salt source, and a trace element source can be provided to the processed distiller's grain.

In some embodiments, the carbon source can include a sugar, (for example, glucose, sucrose, fructose, maltose, xylose, starch, glycerol, or any combination thereof). In some embodiments, the carbon source can be sugars of hydrolyzed lignocellulose. In some embodiments, lignocellulose can be reacted to disconnect the celluloses from the lignin, and then the celluloses can be acid-hydrolyzed to break them down into simple monosaccharides. In some embodiments, the carbon source can be present in about 0.1% to about 20% (w/v) of the culture medium.

In some embodiments, the nitrogen source can include a nitrogen precursor. In some embodiments, the nitrogen precursor can include an amino acid. In some embodiments, the nitrogen source includes amino acids from hydrolyzed proteins. In some embodiments, the nitrogen source can be present in about 0.1% to about 2% (w/v) of the culture medium.

In some embodiments, the salt source can include elements such as magnesium, nitrogen, phosphorus, and sulfur.

In some embodiments, the at least one trace element source can include sodium, calcium, magnesium, iron or zinc.

In some embodiments, the ratio of distiller's grain to the at least one hydrolytic catalyst (defined by solids to liquids) can be a ratio of about 1:5 (w/v) to about 1:30 (w/v), for example, a ratio of 1:5, 1:10, 1:15, 1:20, 1:25, or 1:30, including any range between any two of the proceeding values. In some embodiments, the distiller's grain of 1 g is mixed with about 1 to about 700 enzyme units (U) of the at least one hydrolytic catalyst, e.g., 1, 50, 100, 200, 300, 400, 500, 600, or 700 U, including any range between any two of the proceeding values.

In some embodiments, at least a portion of the mixing the distiller's grain with hydrolytic catalyst can be performed at about 25 degrees Celsius to about 200 degrees Celsius, for example, 25, 50, 75, 100, 150, 175, or 200 degrees Celsius, including any range between any two of the proceeding values. In some embodiments, the at least a portion of the mixing the distiller's grain with the at least hydrolytic catalyst can be performed at about 25 degree Celsius to about 90 degree Celsius. In some embodiments, the majority of the processing occurs at about 25 degrees Celsius or higher.

In some embodiments, the mixing the distiller's grain with the hydrolytic catalyst can be carried out for any amount of time. In some embodiments, it can be carried out for about 30 minutes to about 80 minutes, for example, 30, 40, 50, 60, 70, or 80 minutes, including any range between any two of the proceeding values. In some embodiments, the mixing the distiller's grain with the at least hydrolytic catalyst can be carried out for about 30 minutes to about 48 hours, for example, 30, 60, 120, 240, 480, 1000, 2000, or 3000 minutes, including any range between any two of the proceeding values.

In some embodiments, the hydrolysate can be collected after mixing the distiller's grain with the hydrolytic catalyst. In some embodiments, the hydrolysate can be collected via centrifugation and/or filtration.

In some embodiments, the collected hydrolysate can be further processed. In some embodiments, the pH value of the collected hydrolysate can be adjusted one or more times. In some embodiments, the collected hydrolysate can be detoxified as discussed herein.

In some embodiments, detoxifying the hydrolysate, processed distiller's grain, and/or culture medium can be achieved in any number of ways. In some embodiments, detoxifying can include at least one of adjusting the pH value, incubating, adding and removing an adsorption particle (for example, activated charcoal), and/or adding a detoxifying enzyme. It will be appreciated that these can be employed in any order, at least in part in combination, and/or repeated. In some embodiments, the hydrolysate can be detoxified by adjusting the pH value, incubating, adjusting the pH value a second time, adding an activated charcoal mixing and removing the activated charcoal, and adjusting the pH value a third time.

In some embodiments, the pH value can be adjusted to about 10. In some embodiments, the pH value can be adjusted to about 5. In some embodiments, the pH value can be adjusted to about 10 and then later adjusted to about 5. In some embodiments, detoxification can be achieved under alkaline conditions. Any number of chemicals can be used to adjust the pH value. In some embodiments, the pH value is adjusted by adding at least one of NaOH, $Ca(OH)_2$, and ammonia.

In some embodiments, incubating the hydrolysate can be performed for about 12 hours at about 30 degrees Celsius.

In some embodiments, the detoxifying enzyme can be a laccase enzyme. In some embodiments, about 10% (v/v) of the detoxifying enzyme can be added. In some embodiments, about 2.75 U/mL of the detoxifying enzyme can be added.

As noted above, in some embodiments, detoxifying can include adding and/or removing an adsorption particle. In some embodiments, the adsorption particle includes activated charcoal. In some embodiments, the adsorption particle can be added in about 1% to about 6% (w/v) to the hydrolysate. In some embodiments, the adsorption particle can be added in about 2% to the hydrolysate. In some embodiments, the adsorption particle can be mixed with the hydrolysate for about 5 minutes before removing the adsorption particle from the hydrolysate.

In some embodiments, the detoxification can occur as follows, first, adjusting the pH value of the hydrolysate to 10.0 by NaOH and incubating it at 30 degrees Celsius for 12 hours followed by adjusting the pH value to 5.0 again. Second, adding 1-6% (w/v) activated charcoal into the hydrolysate and mixing them for 5-10 min. Finally, removing the activated charcoal from the hydrolysate and adjusting the pH value to 5.0 again.

In some embodiments, the detoxification can occur as follows, first, adjusting the pH value of the hydrolysate to 10.0 by $Ca(OH)_2$ and incubating it at 30 degrees Celsius for 12 hours followed by adjusting pH value to 5.0 again. Second, adding 2% (w/v) activated charcoal into the hydrolysate and mixing them for 5 min. Finally, removing the activated charcoal from the hydrolysate and adjusting the pH value to 5.0 again.

In some embodiments, the detoxification can occur as follows, first, adjusting the pH value of the hydrolysate to 10.0 by ammonia and incubating it at 30 degrees Celsius for 12 hours followed by adjusting the pH value to 5.0 again. Second, adding 2% (w/v) activated charcoal into the hydrolysate and mixing them for 5 min. Finally, removing the activated charcoal from the hydrolysate and adjusting the pH value to 5.0 again.

In some embodiments, the detoxification can occur as follows, first, adjusting the pH value of the hydrolysate to 5.0 by NaOH and then adding 10% (v/v) laccase (2.75 U/mL) to the hydrolysate. Second, incubating the hydrolysate at 30 degrees Celsius for 12 hours and adjusting the pH value to 5.0 again.

In some embodiments, the detoxification can occur as follows, first, adjusting the pH value of the hydrolysate to 5.0 by $Ca(OH)_2$ and then adding 10% (v/v) laccase (2.75 U/mL) to the hydrolysate. Second, incubating the hydrolysate at 30 degrees Celsius for 12 hours and adjusting the pH value to 5.0 again.

In some embodiments, the detoxification can occur as follows, first, adjusting the pH value of the hydrolysate to 5.0 by ammonia and then adding 10% (v/v) laccase (2.75 U/mL) to the hydrolysate. Second, incubating the hydrolysate at 30 degrees Celsius for 12 hours and adjusting the pH value to 5.0 again.

In some embodiments, any of the above methods can provide a culture medium for bacterial cellulose production. In some embodiments, the medium can include at least one of a maize alcohol fermentation filtrate, a maize alcohol fermentation supernatant, a distiller's grain filtrate, a distiller's grain supernatant, a distiller's grain hydrolysate, or a detoxified distiller's grain hydrolysate. In some embodiments, the medium can further include a carbon source, a nitrogen source, and a salt source. In some embodiments, the medium includes hydrolyzed lignocellulose. In some embodiments, the carbon source can be any of those disclosed herein, for example, cellulose or hemicellulose. In some embodiments, the carbon source comprises a sugar (such as any of those provided herein).

In some embodiments, the carbon source is present at about 0.1 to about 20% (w/v) of the amount of at least one of the maize alcohol fermentation filtrate, the maize alcohol fermentation supernatant, a distiller's grain filtrate, a distiller's grain supernatant, the distiller's grain hydrolysate, or the detoxified distiller's grain hydrolysate.

In some embodiments, the nitrogen source is present at about 0.1 to about 2% (w/v) of the amount of at least one of the maize alcohol fermentation filtrate, the maize alcohol fermentation supernatant, a distiller's grain filtrate, a distiller's grain supernatant, the distiller's grain hydrolysate, or the detoxified distiller's grain hydrolysate.

In some embodiments, the carbon source includes a sugar that is present in an amount of about 0.1 to about 20% (w/v) the amount of the detoxified distiller's grain hydrolysate, and wherein the nitrogen source is present at about 0.1 to about 2% (w/v) of the amount of the detoxified distiller's grain hydrolysate. In some embodiments, distiller's grain includes residual ethanol and/or yeast. In some embodiments, grain does not include residual ethanol and/or yeast.

Figure 2:
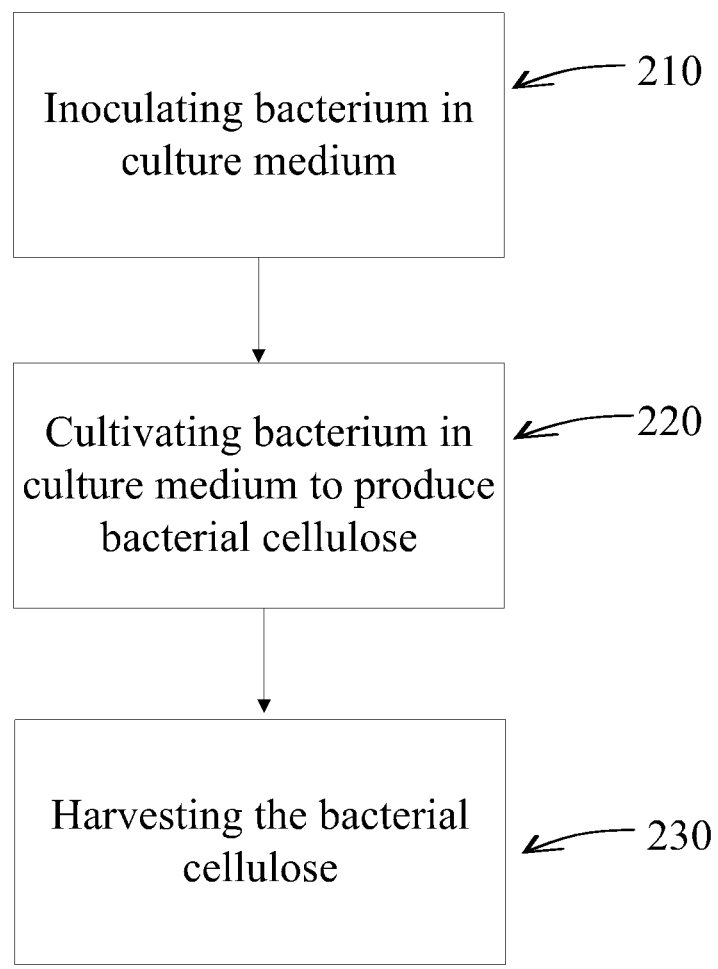
FIG. 2 is a flowchart depicting some embodiments of a method of producing bacterial cellulose.

As shown in FIG. 2, in some embodiments, a method of producing bacterial cellulose is provided. In some embodiments, the method includes inoculating at least one bacterium in a culture medium (block 210). In some embodiments, the method includes cultivating the at least one bacterium in the culture medium (block 220). In some embodiments, the cultured bacterium can produce bacterial cellulose. In some embodiments, the method optionally includes harvesting the bacterial cellulose (block 230).

In some embodiments, the culture medium can be any medium embodiment as provided herein. In some embodiments, the culture medium includes a distiller's grain hydrolysate and/or a processed distiller's grain or product thereof. In some embodiments, the hydrolysate includes at least one of an enzymatically created hydrolysate and/or a detoxified acid created hydrolysate. It will be appreciated that, in some embodiments, the bacterium are efficient when supplied with an abundant carbon source and minimal nitrogen source.

In some embodiments, when bacterial cellulose production is desired, the at least one bacterium can be selected from any suitable bacterium capable of producing bacterial cellulose. In some embodiments, the bacterium can be at least one of a Gram-negative bacteria species such as *Acetobacter, Azotobacter, Rhizobium, Pseudomonas, Salmonella, Alcaligenes*, or Gram-positive bacteria species such as *Sarcina ventriculi* or Agro bacterium. In some embodiments, the bacterium can include *A. xylinum, A. hansenii*, and/or *A. pasteurianus*. In some embodiments, the bacterium can be an acetic acid bacterium. In some embodiments, the bacterium can be *Gluconacetobacter xylinus*.

In some embodiments, bacteria are inoculated into the culture medium using standard procedures. In some embodiments, the bacteria are raised until they achieve a concentration of about 5% to about 10% (v/v).

In some embodiments, any form of cultivating the bacterium for bacterial cellulose production can be employed.

Parameters for cultivating the bacterium can be adjusted to achieve a desired yield. In some embodiments, the temperature, duration and/or mixing speed can be adjusted. In some embodiments, at least a portion of the cultivating is performed at about 20 degrees Celsius to about 37 degrees Celsius, for example, 20, 25, 28, 30, 32, 35 or 37 degrees Celsius, including any range between any two of the proceeding values. In some embodiments, the bacterium can be cultured for about 1 to about 20 days, for example, 1, 3, 5, 7, 9, 11, or 20 days, including any range between any two of the proceeding values. In some embodiments, the bacterium can be cultured in a reactor or statically in an incubator. In some embodiments, cultivating the bacterium includes mixing the bacterium at about 160 rpm to about 250 rpm.

In some embodiments, production of the bacterial cellulose can be performed using the filtrate and/or supernatant after the separation of distiller's grain, which can be used directly as the nutrients of culture medium supplemented with sugars (1-100%), nitrogen source (0.1-2%), some salts (0.1-3%) and trace elements (0.01-0.1%).

In some embodiments, production of the bacterial cellulose can be performed using the enzymatic hydrolysate and/or the detoxified acid hydrolysate of WDG or DDG or DDGS, which can be used as the nutrients of culture medium supplemented with sugars (1-100%), nitrogen source (0.1-2%), some salts and trace elements.

In some embodiments, production of the bacterial cellulose can be performed using the filtrate or supernatant, which can be mixed with the enzymatic hydrolysate and/or the detoxified acid hydrolysate of WDG or DDG or DDGS, and the mixture can be used as the nutrients of culture medium supplemented with sugars (1-100%), nitrogen source (0.1-2%), some salts (0.1-3%) and trace elements (0.01-0.1%).

In some embodiments, production of the bacterial cellulose can include inoculating the producing bacteria into the culture medium, which can be autoclaved at about 105 to about 121 degrees Celsius for about 15 to about 30 minutes and/or sterilized by filtration with sterile filters until the composition is about 5%-10% (w/v) and then cultured at about 20 to about 37 degrees Celsius and about 160 to about 250 rpm and/or cultured statically in an incubator at about 20 to about 37 degrees Celsius for about 3 to 20 days, and then the bacterial cellulose is harvested.

Distiller's Grains (DG) are a cereal byproduct of the ethanol production process and dried from Wet Distiller's Grains (WDG), which contain primarily unfermented grain residues (protein, fiber, fat and up to 70% moisture). Distiller's grains are rich in cereal and residual yeast protein, minerals and vitamins. There are a variety of sources for these grains, including brewers and ethanol plants. Distiller's grain can be created in distilleries by drying mash. DG can be divided into two parts, DDG (Dried Distiller's Grains) and DDGS (Dried Distiller's Grains with Solubles), which are the dried residues remaining after the starch portion of the grain is fermented in the ethanol production process with selected yeasts and enzymes to produce ethanol and carbon dioxide. As outlined herein, any of these forms of distiller's grains can be used for producing bacterial cellulose by hydrolysis to sugars and amino acids.

Example 1

Method of Making a Hydrolysate from Distiller's Grain

The present example outlines how to prepare hydrolysate from distiller's grain using an acid.

Dried distiller's grain (DDG) from a maize ethanol fermentation, which contains residual ethanol, fat, some heavy metal ions and large amount of cellulose, hemicellulose and protein is provided and treated. The treatment includes separation, filtration, centrifugation, and drying.

The processed DDG is mixed with 0.4% w/v HCl for 12 hours in a reaction container. The ratio of solid DDG to liquid acid is 1:10. The mixture is held at a temperature of 50 degrees Celsius for 50 minutes to form an acid processed hydrolysate. The residual slag of the distiller's grain and the acid hydrolysate are separated, and the hydrolysate is collected and refrigerated, thereby providing a hydrolysate from the distiller's grain.

Example 2

Method of Making Hydrolysate from Distiller's Grain

The present example outlines how to prepare a hydrolysate from distiller's grain enzymatically.

Dried distiller's grain (DDG) from a maize ethanol fermentation is provided and treated. The treatment includes separation, filtration, and centrifugation. The supernatant is collected and dried. The concentration of total reducing sugar in the filtrate or supernatant can be assayed by 3,5-dinitrosalicylic acid (DNS) method (Miller, 1959) with D-glucose as the standard.

The DDG of 1 g is mixed with 500 U of xylanase. The ratio of solid DDG to liquid enzyme is 1:10. The mixture is held at 70 degrees Celsius for 20 hours to produce the hydrolysate. The residual slag of the distiller's grain and the enzymatic hydrolysate are separated, and the hydrolysate is collected and refrigerated.

Example 3

Detoxification of the Hydrolysate

The present example outlines how to detoxify the hydrolysate from Example 1 for further use in process such as bacterial cellulose production.

First the pH value of the hydrolysate is adjusted to 10.0 using NaOH. The hydrolysate is incubated at 30 degrees Celsius for 12 hours. The pH value is then adjusted to 5.0. Activated charcoal, 1-6% (w/v), is added to the hydrolysate and mixed for 5-10 minutes. The activated charcoal is then removed from the hydrolysate and the pH value to adjusted 5.0. The method thereby removes at least some of the toxins from the hydrolysate product of Example 1.

Example 4

Detoxification of Acid Hydrolysate

The present example discloses another method to detoxify the hydrolysate from Example 1.

First the pH value of the hydrolysate is adjusted to 5.0 using NaOH. 10% (v/v) laccase (2.75 U/mL) is added to the hydrolysate. The hydrolysate is incubated at 30 degrees Celsius for 12 hours and the pH value is adjusted to 5.0. The method thereby removes at least some of the toxins from the hydrolysate product of Example 1.

Example 5

Production of Bacterial Cellulose

The present example outlines how to produce bacterial cellulose using the culture medium provided herein.

The bacteria (*Gluconacetobacter xylinus* ATCC 23770) to be used for producing cellulose are inoculated into the culture medium of Examples 2, 3, or 4 that autoclaved at 115 degrees Celsius for 30 min. The mixture is then cultured at 30 degrees Celsius at 160 rpm for 15 days to allow the bacteria to produce bacterial cellulose. The bacterial cellulose is then harvested. The yield of BC ranges from 1 g/L to 5 g/L. If the mixture is cultured at 30 degrees Celsius statically for 15 days to allow the bacteria to produce bacterial cellulose, the yield of BC ranges from 6 g/L to 32 g/L.

As an alternative, 0.3% peptone, 0.5% yeast extract, and 2.5% glucose (w/v) can be added to the culture medium of Examples 2, 3, or 4.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A culture medium for bacterial cellulose production mixture, the culture medium comprising:
   a detoxified distiller's grain hydrolysate;
   a carbon source; wherein the carbon source is present from about 0.1% (w/v) to 20% (w/v) of the detoxified distiller's grain hydrolysate;
   a nitrogen source;
   a salt source;
   a bacterium capable of producing bacterial cellulose; and
   bacterial cellulose.

2. The bacterial cellulose production mixture of claim 1, wherein the carbon source comprises sugars of hydrolyzed lignocellulose.

3. The bacterial cellulose production mixture of claim 1, wherein the carbon source includes at least one of cellulose or hemicellulose.

4. The bacterial cellulose production mixture of claim 1, wherein the carbon source comprises a sugar.

5. The bacterial cellulose production mixture of claim 1, further comprising at least one of a maize alcohol fermentation filtrate, a maize alcohol fermentation supernatant, a distiller's grain filtrate, a distiller's grain supernatant, or a distiller's grain hydrolysate; wherein the carbon source is present at about 0.1% (w/v) to about 20% (w/v) of the amount of at least one of the maize alcohol fermentation filtrate, the maize alcohol fermentation supernatant, the distiller's grain filtrate, the distiller's grain supernatant, or the distiller's grain hydrolysate.

6. The bacterial cellulose production mixture of claim 1, wherein the nitrogen source is present at about 0.1% (w/v) to about 2% (w/v) of the amount of the detoxified distiller's grain hydrolysate.

7. The bacterial cellulose production mixture of claim 1, further comprising at least one of a maize alcohol fermentation filtrate, a maize alcohol fermentation supernatant, a distiller's grain filtrate, a distiller's grain supernatant, or a distiller's grain hydrolysate.

8. The bacterial cellulose production mixture of claim 1, wherein the at least one bacterium capable of producing bacterial cellulose includes at least one of *Acetobacter, Azotobacter, Rhizobium, Pseudomonas, Salmonella, Alcaligenes, Sarcina ventriculi, Agrobacterium, xylinum, A. hansenii, A. pasteurianus,* or *Gluconacetobacter xylinus.*

9. A culture medium for bacterial cellulose production mixture, the culture medium comprising:
   a detoxified distiller's grain hydrolysate;
   a carbon source including a sugar that is present in an amount of about 0.1% (w/v) to about 20% (w/v) the amount of the detoxified distiller's grain hydrolysate;
   a nitrogen source present at about 0.1% (w/v) to about 2% (w/v) of the amount of the detoxified distiller's grain hydrolysate;
   a salt source;
   a bacterium capable of producing bacterial cellulose; and
   bacterial cellulose.

10. The bacterial cellulose production mixture of claim 9, further comprising at least one of a maize alcohol fermentation filtrate, a maize alcohol fermentation supernatant, a distiller's grain filtrate, a distiller's grain supernatant, or a distiller's grain hydrolysate.

11. The bacterial cellulose production mixture of claim 9, wherein the carbon source comprises sugars of hydrolyzed lignocellulose.

12. The bacterial cellulose production mixture of claim 9, wherein the carbon source further includes at least one of cellulose or hemicellulose.

13. The bacterial cellulose production mixture of claim 9, wherein the at least one bacterium capable of producing bacterial cellulose includes at least one of *Acetobacter, Azotobacter, Rhizobium, Pseudomonas, Salmonella, Alcaligenes, Sarcina ventriculi, Agrobacterium, xylinum, A. hansenii, A. pasteurianus,* or *Gluconacetobacter xylinus.*

14. A method of producing bacterial cellulose, the method comprising:
   inoculating at least one bacterium capable of producing bacterial cellulose in a bacterial cellulose production mixture comprising:
   a detoxified distiller's grain hydrolysate;
   a carbon source; wherein the carbon source is present from about 0.1% (w/v) to 20% (w/v) of the detoxified distiller's grain hydrolysate;
   a nitrogen source; and
   a salt source
   cultivating the at least one bacterium capable of producing bacterial cellulose in the bacterial cellulose production mixture to produce bacterial cellulose; and
   harvesting the bacterial cellulose.

15. The method of claim 14, wherein the bacterial cellulose production mixture further comprises a distiller's grain hydrolysate.

16. The method of claim 15, wherein the hydrolysate includes at least one of an enzymatic hydrolysate or a detoxified acid hydrolysate.

* * * * *

UNITED STATES PATENT AND TRADEMARK OFFICE
CERTIFICATE OF CORRECTION

PATENT NO. : 9,708,580 B2
APPLICATION NO. : 13/885390
DATED : July 18, 2017
INVENTOR(S) : Hong It is certified that error appears in the above-identified patent and that said Letters Patent is hereby corrected as shown below:

In the Specification

In Column 2, Line 65, delete "(DOGS)," and insert -- (DDGS), --, therefor.

In Column 9, Line 59, delete "recitation no" and insert -- recitation, no --, therefor.

In the Claims

In Column 12, Line 38, in Claim 14, delete "a salt source" and insert -- a salt source; --, therefor.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*